United States Patent [19]
Waranis et al.

[11] Patent Number: 5,530,006
[45] Date of Patent: Jun. 25, 1996

[54] RAPAMYCIN FORMULATION FOR IV INJECTION

[75] Inventors: Robert P. Waranis, Chazy, N.Y.; Maureen M. Harrison, St. Albans, Vt.; Thomas W. Leonard, Plattsburgh; Robin P. Enever, Rouses Point, both of N.Y.

[73] Assignee: American Home Products Corporation, Madison, N.J.

[21] Appl. No.: 207,325

[22] Filed: Mar. 7, 1994

Related U.S. Application Data

[63] Continuation-in-part of Ser. No. 860,530, Mar. 30, 1992, abandoned.

[51] Int. Cl.$^6$ .................................................. A61K 31/44
[52] U.S. Cl. ................. 514/291; 540/456; 424/78.31; 424/78.32
[58] Field of Search ................. 514/28, 291; 540/456; 424/78.31, 78.32

[56] References Cited

U.S. PATENT DOCUMENTS

| | | |
|---|---|---|
| 3,627,886 | 12/1971 | Newmark . |
| 3,929,992 | 12/1975 | Sehgal . |
| 5,202,241 | 4/1993 | Selia et al. ............................ 435/71.3 |

FOREIGN PATENT DOCUMENTS

| | | | |
|---|---|---|---|
| 041795 | 12/1981 | European Pat. Off. ......... | A61K 9/00 |
| 202837 | 11/1986 | European Pat. Off. ......... | A61K 9/10 |
| 444659 | 9/1991 | European Pat. Off. ....... | A61K 31/71 |

OTHER PUBLICATIONS

Venkataramanan, R., Transplantation Proceedings, 22(1), Suppl. 1, 52–56 (1990).
Physicnans' Desk Ref., 45th ed., 1991, pp. 1961–1964.
Martel, R., Can. Jour. of Physiological Pharm. 55, 48–51 (1977).

*Primary Examiner*—Elli Peselev
*Attorney, Agent, or Firm*—Arthur G. Seifert

[57] ABSTRACT

Disclosed herein is an aqueous, injectable rapamycin solution comprising 0.1 to 10 percent of a concentrate solution of rapamycin in N,N-dimethylacetamide, at concentrations of rapamycin ranging from 0.25 mg/ml to 100 mg/ml, in combination with a diluent solution consisting of 0.1 to 10 weight percent of one or more polyoxyethylene sorbitan esters, 10 to 60 weight percent of either polyethylene glycol 200 or 300 or both and 30 to 90 volume percent water, wherein the concentration of rapamycin in he combined solution ranges from 0.05 mg/ml to 5.0 mg/ml. Also disclosed is an aqueous, injectable solution of rapamycin, said solution comprising rapamycin in 0.1 to 10 weight percent N,N-dimethylacetamide, 0.09 to 7.5 weight percent of one or more polyoxyethylene sorbitan esters, 9 to 60 weight percent of either polyethylene glycol 200 or 300 or both and 30 to 90 volume percent of water, wherein the concentration of rapamycin in the solution ranges from 0.05 mg/ml to 5.0 mg/ml. Preferred aqueous, injectable rapamycin solutions are those wherein one polyoxyethylene sorbitan ester is present and the polyethylene glycol present is polyethylene glycol 300.

17 Claims, No Drawings

RAPAMYCIN FORMULATION FOR IV INJECTION

This is a continuation-in-part application of application U.S. Ser. No. 07/860,530 filed Mar. 30, 1992, now abandoned.

The invention disclosed herein provides an aqueous formulation of rapamycin for intravenous injection (iv). In one aspect the invention comprises a concentrate solution of rapamycin in N,N-dimethylacetamide, in combination with a diluent consisting of a polyoxyethylene sorbitan ester, polyethylene glycol 300 and water, all in given proportions as described below.

BACKGROUND OF THE INVENTION

Rapamycin is a macrolide antiobiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arof Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin is insoluble in water and is only slightly soluble in solubilizers, such as propylene glycol, glycerin and PEG 400, commonly used in preparing parenteral formulations. It is only sparingly soluble in PEG 20 and 300 and is insoluble or very slightly soluble in commonly used aqueous injectable co-solvent systems, such as, 20% ethanol/water, 10% DMA/water, 20% Cremophar EL®/water and 20% polysorbate 80/water. For these reasons commercially acceptable injectable formulations of rapamycin have been difficult to make. An injectable composition of rapamycin is described in European Patent Publication No. 0041795, published Dec. 16, 1981. In this injectable formulation rapamycin is first dissolved in a low boiling point organic solvent, namely, acetone, methanol or ethanol. This solution is then mixed with a nonionic surfactant selected from polyoxyethylated fatty acids; polyoxyethylated fatty alcohols; and polyoxyethylated glycerin hydroxy fatty acid esters, e.g. polyoxyethylated caster oil, exemplified by Cremophor® EL and polyoxyethylated hydrogenated castor oil, exemplified by Cremophor® RH 40 and Cremophor® RH60. Cremophor® EL is the primary nonionic surfactant used in the examples.

The primary immunosuppressive agent presently used for inhibiting rejection in the allograft transplantation of organs in man is cyclosporine (Sandimmune®). Cyclosporine is a cyclic polypeptide consisting of 11 amino acids. The intravenous injectable formulation of Sandimmune® (IV) is a sterile ampul containing, per ml, 50 mg of cyclosporine, 650 mg of Cremophor® EL and alcohol Ph Helv. (32.9% by volume) (under nitrogen). For administration this mixture is diluted further with 0.9% Sodium Chloride Injection or 5% Dextrose Injection before use. (*Physician's Desk Reference*, 45th ed., 1991, pp. 1962–64, Medical Economics Company, Inc.) The macrolide molecule designated FK506, which has certain structural similarities to rapamycin, is also currently undergoing clinical investigation for inhibiting rejection in allograft organ transplantation in man. FK506 is isolated from *Streptomyces tsuskubaensis* and is described in U.S. Pat. No. 4,894,366 to Okuhara et al., issued Jan. 16, 1990 R. Venkataramanan et al., in Transplantation Proceedings, 22, No. 1, Suppl., 1 pp 52–56 (February 1990), report that the intravenous injectable formulation of FK506 is provided as a 10 mg/ml solution of FK506 in polyoxyethylated castor oil (HCO-60, a surfactant) and alcohol. The intravenous preparation must be diluted with saline or dextrose and administered as an infusion for 1 to 2 hours.

DETAILED DESCRIPTION OF THE INVENTION

One aspect of this invention is an aqueous-based, injectable rapamycin solution comprising a concentrate solution of rapamycin in N,N-dimethylacetamide (DMA) in combination with a diluent solution comprising a polyoxyethylene sorbitan ester, polyethylene glycol 300 and water. Specifically, Applicants' invention is an aqueous, injectable rapamycin solution comprising 0.1 to 10 weight percent of a concentrate solution of rapamycin in N,N-dimethylacetamide, at concentrations of rapamycin ranging from 0.25 mg/ml to 100 mg/ml, in combination with a diluent solution consisting of 0.1 to 10 weight percent of one or more polyoxyethylene sorbitan esters, 10 to 60 weight percent of either polyethylene glycol 200 or 300 or both and 30 to 90 volume percent water, wherein the concentration of rapamycin in the combined solution ranges from 0.05 mg/ml to 5.0 mg/ml. Preferred aqueous, injectable rapamycin solutions are those wherein one polyoxyethylene sorbitan ester is present and the polyethylene glycol present is polyethylene glycol 300.

Preferred aqueous, injectable rapamycin solutions of this aspect of the invention are those in which the concentration of rapamycin in the N,N-dimethylacetamide concentrate ranges from 0.5 mg/ml to 50 mg/ml. More preferred are those in which the concentration of rapamycin in the N,N-dimethylacetamide concentrate ranges from 5.0 mg/ml to 50 mg/ml. Also preferred aqueous, injectable rapamycin solutions of the invention are those in which the concentration of rapamycin in the combination solution ranges from 0.1 mg/ml to 4 mg/ml and those wherein the N,N-dimethylacetamide concentrate of rapamycin comprises 0.2 to 8 weight percent of the total solution.

Further preferred aqueous, injectable rapamycin solutions of the invention are those in which the diluent consists of 1.0 to 8 weight percent polyoxyethylene sorbitan ester, 10 to 50 percent polyethylene glycol 300, and 40 to 90 volume percent of water. Also preferred are aqueous, injectable rapamycin solutions of the invention in which 30 to 90 percent by volume of the total solution is water.

Especially preferred aqueous, injectable rapamycin solutions according to this aspect of the invention comprise 0.2 to 8 weight percent of a concentrate solution of rapamycin in N,N-dimethylacetamide, at concentrations of rapamycin ranging from 5 mg/ml to 50 mg/ml, in combination with a diluent solution consisting of 1.0 to 8 weight percent of a polyoxyethylene sorbitan ester, 10 to 50 weight percent polyethylene glycol 300 and 40 to 90 volume percent water, wherein the concentration of rapamycin in the combined solution ranges from 0.1 mg/ml to 4.0 mg/ml.

A second aspect of this invention is an aqueous, injectable solution of rapamycin, said solution comprising rapamycin in 0.1 to 10 weight percent N,N-dimethylacetamide, 0.09 to 7.5 weight percent of one or more polyoxyethylene sorbitan esters, 9 to 60 weight percent of either polyethylene glycol 200 or 300 or both and 30 to 90 volume percent water, wherein the concentration of rapamycin in the solution range from 0.05 mg/ml to 5.0 mg/ml. Preferred aqueous, injectable rapamycin solutions are those wherein one polyoxyethylene sorbitan ester is present and the polyethylene glycol present is polyethylene glycol 300.

Preferred aqueous, injectable rapamycin solutions of this aspect of the invention are those wherein the concentration of rapamycin in the solution ranges from 0.1 mg/ml to 4 mg/ml. Also preferred, independently, are those wherein the N,N-dimethylacetamide comprises 0.2 to 8 weight percent of the solution, the polyoxyethylene sorbitan ester comprises 2 to 7.5 percent by weight, the polyethylene glycol 300 comprises 10 to 50 weight percent of the solution, and water comprises 30 to 90 percent by volume of the total solution.

Especially preferred aqueous, injectable solutions of rapamycin, of this aspect of the invention comprise rapamycin in 2 to 8 weight percent N,N-dimethylacetamide, 2 to 7.5 weight percent of a polyoxyethylene sorbitan ester, 10 to 50 weight percent polyethylene glycol 300 and 36 to 86 volume percent of water, wherein the concentration of rapamycin in the solution ranges from 0.1 mg/ml to 4.0 mg/ml.

The aqueous, injectable rapamycin solutions of the invention are preferred for administration by bolus injection, rather than by infusion, particularly for such solutions where the concentration of rapamycin in the combined solution is greater than 0.1 mg/ml. An infusion period of less than 24 hours is preferred. An infusion period of one-quarter hour to 6 hours is particularly preferred.

The manufacture of rapamycin iv concentrate comprises adding the rapamycin to the DMA and mixing until a solution results, which may be accomplished at room temperatures. The solution is then filtered in a known manner for sterility. Appropriate volumes of the concentrate solution are filled into ampules which are then sealed in a known manner. In accordance with standard manufacturing procedures for injectables, sterile conditions are maintained throughout the filtering, filling and sealing operations. The product rapamycin concentrate is best stored under refrigeration.

The manufacture of each of the rapamycin iv diluent systems comprises weighing the polysorbate 80 into a suitable container, adding the appropriate amounts of PEG 300 and water for injection and mixing until a solution results. Appropriate volumes of diluent are filled into vials which are then stoppered, sealed and autoclaved. The completed rapamycin diluent solution may be stored at room temperature or under refrigeration.

The procedure for constituting the final formulas for administration comprises injecting an aliquot of rapamycin iv concentrate into a vial containing the rapamycin iv diluent, shaking for approximately one minute or until a clear solution results. The constituted solution should be administered within the stated use period. The use period of constituted rapamycin injectable solutions is the period of time during which the constituted solution remains clear and colorless. The use period may range up to 4 hours, but a use period of 1 hour is preferred.

Preferred polyoxyethylene sorbitan esters are polysorbate 20, 60 or 80, of which polysorbate 80 is particularly preferred. DMA, polysorbate 80 and PEG 300 are readily available commercial products for use in pharmaceutical manufacturing. DMA may be obtained from EM Science of Gibbstown, N.J. PEG 300 may be obtained from J. T. Baker Inc. of Phillipsburg, N.J., and polysorbate 80 may be obtained from ICI America, Inc of Wilmington, Del.

The following examples further illustrate the practice of the invention.

EXAMPLE 1

Preparation of Rapamycin IV Concentrate in Dimethylacetamide (50 mg/ml)

Rapamycin IV Concentrate in Dimethylacetamide (50 mg/ml)
Formula (Density - 0.944 g/ml):

| Ingredients | | Amount |
| --- | --- | --- |
| Rapamycin @ 100% | | 5.0 gm |
| Dimethylacetamide (DMA) | qs | 100 ml or 94.4 gm |

Procedure:
1. Weigh the rapamycin into a suitable calibrated container.
2. Adjust volume to 100 ml with DMA.
3. Mix until a uniform solution results.
4. Sterile filter the solution.
5. Package into ampules and seal.

EXAMPLE 2

Preparation of Rapamycin IV Solution at 2.0 mg/ml

A. Diluent for Rapamycin IV at 2.0 mg/ml
Formula (Density - 1.081 gm/ml):

| Ingredients | | Amount |
| --- | --- | --- |
| Polysorbate 80, NF | | 4.0 gm |
| Polyethylene Glycol 300, NF | | 50.0 gm |
| Water for Injection, USP | qs | 100 ml or 108.1 gm |

Procedure:
1. Weigh the Polysorbate 80 into a suitable calibrated container.
2. Add the Polyethylene Glycol 300 to the container in Step #1.
3. Adjust to final volume with Water for Injection, USP.
4. Mix until uniform.
5. Filter the resulting solution.
6. Fill 12.0 ml±0.1 ml into each 20 ml flint vial, seal and crimp.
7. Autoclave to achieve sterility.

B. Rapamycin IV solution at 2.0 mg/ml (constituted)
Formula (Density - 1.077 gm/ml):

| Ingredients | Amount |
| --- | --- |
| Rapamycin IV Concentrate @ 50 mg/ml | 0.5 ml |
| Diluent for IV-Rapamycin | 12.0 ml |

Procedure:
1. Inject 0.5 ml of Rapamycin IV Concentrate at 50 mg/ml into a vial container 12.0 ml of diluents for IV-Rapamycin using good sterile technique.
2. Shake until a clear solution results.

EXAMPLE 3

Preparation of Rapamycin IV Solution at 4.0 mg/ml

A. Diluent for Rapamycin IV at 4.0 mg/ml
Formula (Density - 1.077 gm/ml):

| Ingredients | | Amount |
|---|---|---|
| Polysorbate 80, NF | | 8.0 gm |
| Polyethylene Glycol 300, NF | | 50.0 gm |
| Water for Injection, USP | qs | 100 ml or 107.7 gm |

Procedure:
1. Weigh the Polysorbate 80 into a suitably calibrated container.
2. Add the Polyethylene Glycol 300 to the container in Step #1.
3. Adjust to final volume with Water for Injection, USP
4. Mix until uniform.
5. Filter the resulting solution.
6. Fill 5.75 ml±0.1 ml into each 10 ml flint vial, seal and crimp.
7. Autoclave to achieve sterility.

B. Rapamycin IV solution at 4.0 mg/ml (constituted)
Formula (Density - 1.072 gm/ml):

| Ingredients | Amount |
|---|---|
| Rapamycin IV Concentrate @ 50 mg/ml | 0.5 ml |
| Diluent for IV-Rapamycin | 5.75 ml |

Procedure:
1. Inject 0.5 ml of Rapamycin IV Concentrate at 50 mg/ml into a vial container 5.75 ml of diluent for IV-Rapamycin using good sterile technique.
2. Shake until a clear solution results.

EXAMPLE 4

The examples herein represent the batch production of ampules of rapamycin concentrate and vials of diluent for use in obtaining 0.1, 0.5, 2.0 and 4.0 mg/mL. The rapamycin iv solutions may be constituted for injection in the same manner as in Examples 2B and 3B.

A. Rapamycin IV Concentrate 50 mg/ml

| | Claim/mL | Input/ Ampule | Representative Batch Formula 10,000 Ampules |
|---|---|---|---|
| Active Ingredient Rapamycin @ 100% | 0.050 g | 0.0325 g | 0.325 kg |
| Inactive Ingredients: Dimethylacetamide qs ad Density = 0.944 g/mL | | 0.65 mL or 0.61 g | 6.50 L or 6.14 kg |

B. Diluent for Rapamycin IV at 0.1 mg/mL

| Active Ingredient | Input/Vial | Representative Batch Formula 10,000 Vials |
|---|---|---|
| Polysorbate 80, NF | 4.00 g | 40.0 kg |
| Polyethylene Glycol 300, NF | 50.0 g | 500 kg |
| Water for Injection, USP qs ad | 100 mL or 108 g | 1000 L or 1081 kg |
| Density - 1.081 g/mL | | |

C. Diluent for Rapamycin IV at 0.5 mg/mL

| Active Ingredient | Input/Vial | Representative Batch Formula 10,000 Vials |
|---|---|---|
| Polysorbate 80, NF | 2.00 g | 20.0 kg |
| Polyethylene Glycol 300, NF | 25.0 g | 250 kg |
| Water for Injection, USP qs ad | 50.0 mL or 54.1 g | 500 L or 541 kg |
| Density - 1.081 g/mL | | |

D. Diluent for Rapamycin IV at 2 mg/mL

| Active Ingredient | Input/Vial | Representative Batch Formula 10,000 Vials |
|---|---|---|
| Polysorbate 80, NF | 0.480 g | 4.80 kg |
| Polyethylene Glycol 300, NF | 6.00 g | 60.0 kg |
| Water for Injection, USP qs ad | 12.0 mL or 13.0 g | 120 L or 130 kg |
| Density - 1.081 g/mL | | |

E. Diluent Rapamycin IV at 4 mg/mL

| Active Ingredient | Input/Vial | Representative Batch Formula 10,000 Vials |
|---|---|---|
| Polysorbate 80, NF | 0.460 g | 4.60 kg |
| Polyethylene Glycol 300, NF | 2.88 g | 28.8 kg |
| Water for Injection, USP qs ad | 5.75 mL or 6.19 g | 57.5 L or 61.9 kg |
| Density - 1.077 g/mL | | |

Note:
A–E If the potency of rapamycin is less than 100%, the input must be adjusted to give claim potency.

Procedures for preparations A–E.
A. Rapamycin IV Concentrate at 50 mg/ml Procedure:
1. Weigh the rapamycin into a suitable calibrated container.
2. Add Dimethylacetamide to achieve the appropriate volume or weight
3. Mix until a solution results.
4. Maintain sterile conditions throughout filtering, filling and sealing.
5. Filter the solution from Step #3 through a 0.2 micron filter.
6. Fill 0.65 ml±0.05 ml (0.61 g+0.05 g) of the solution from Step #5 into each 1 ml amber ampule and seal
7. Store under refrigeration.
B. Rapamycin IV Diluent at 0.1 mg/ml Procedure:
1. Weigh the Polysorbate 80 into a suitable container.
2. Add the appropriate weight of the Polyethylene Glycol 300 to the container in Step #1.
3. Add Water for Injection to achieve the appropriate volume or weight.
4. Mix until a solution results.
5. Filter the solution from Step #4 through a 0.2 micron filter.
6. Fill 100 mL±2 mL (108 g±2.2 g) of the solution from Step #5 into each 100 mL flint vial, seal with a barrier faced stopper and crimp with an aluminum seal.
7. Sterilize by steam autoclave.
8. Store at room temperature or under refrigeration.
C. Rapamycin IV Diluent at 0.5 mg/ml Procedure:
1. Weigh the Polysorbate 80 into a suitable container.
2. Add the appropriate weight of the Polyethylene Glycol 300 to the container in Step #1.
3. Add Water for Injection to achieve the appropriate volume or weight.
4. Mix until a solution results.

5. Filter the solution from Step #4 through a 0.2 micron filter.
6. Fill 50 mL±1 mL (54 g±1.1 g) of the solution from Step #5 into each 100 mL flint vial, seal with a barrier faced stopper and crimp with an aluminum seal.
7. Sterilize by steam autoclave.
8. Store at room temperature or under refrigeration.

D. Rapamycin IV Diluent at 2 mg/ml Procedure:
1. Weigh the Polysorbate 80 into a suitable container.
2. Add the appropriate weight of the Polyethylene Glycol 300 to the container in Step #1.
3. Add Water for Injection to achieve the appropriate volume or weight.
4. Mix until a solution results.
5. Filter the solution from Step #4 through a 0.2 micron filter.
6. Fill 12.0 mL±0.1 mL (13.0 g±0.1 g) of the solution from Step #5 into each 20 mL flint vial, seal with a barrier faced stopper and crimp with an aluminum seal.
7. Sterilize by steam autoclave.
8. Store at room temperature or under refrigeration.

E. Rapamycin IV Diluent at 4 mg/ml Procedure:
1. Weigh the Polysorbate 80 into a suitable container.
2. Add the appropriate weight of the Polyethylene Glycol 300 to the container in Step #1.
3. Add Water for Injection to achieve the appropriate volume or weight.
4. Mix until a solution results.
5. Filter the solution from Step #4 through a 0.2 micron filter.
6. Fill 5.75 mL±0.1 mL (6.2 g±0.1 g) of the solution from Step #5 into each 10 mL flint vial, seal with a barrier faced stopper and crimp with an aluminum seal.
7. Sterilize by steam autoclave.
8. Store at room temperature or under refrigeration.

What we claim is:

1. An aqueous, injectable rapamycin solution consisting essentially of 0.1 to 10 percent of a concentrate solution of rapamycin in N,N-dimethylacetamide, at concentrations of rapamycin ranging from 0.25 mg/ml to 100 mg/ml, in combination with a diluent solution consisting essentially of 0.1 to 10 weight percent of one or more polyoxyethylene sorbitan esters, 10 to 60 weight percent of either polyethylene glycol 200 or 300 or both and 30 to 90 volume percent water, wherein the concentration of rapamycin in the combined solution ranges from 0.05 mg/ml to 5.0 mg/ml.

2. An aqueous, injectable rapamycin solution according to claim 1 wherein one polyoxyethylene sorbitan ester is present and the polyethylene glycol present is polyethylene glycol 300.

3. An aqueous, injectable rapamycin solution according to claim 2 wherein the concentration of rapamycin in the N,N-dimethylacetamide concentrate ranges from 0.5 mg/ml to 50 mg/ml.

4. An aqueous, injectable rapamycin solution according to claim 2 wherein the concentration of rapamycin in the N,N-dimethylacetamide concentrate ranges from 5.0 mg/ml to 50 mg/ml.

5. An aqueous, injectable rapamycin solution according to claim 2, for bolus injection, wherein the concentration of rapamycin in the combination solution ranges from 0.1 mg/ml to 4 mg/ml.

6. An aqueous, injectable rapamycin solution according to claim 2 wherein the N,N-dimethylacetamide concentrate of rapamycin ranges from 0.2 to 8 percent of the total solution.

7. An aqueous, injectable rapamycin solution according to claim 2 wherein the diluent consists essentially of 1.0 to 8 percent polyoxyethylene sorbitan ester, 10 to 50 percent polyethylene glycol 300, and 40 to 90 volume percent of water.

8. An aqueous, injectable rapamycin solution according to claim 2 wherein 30 to 90 percent by volume of the total solution is water.

9. An aqueous, injectable rapamycin solution according to claim 2, for bolus injection, consisting essentially of 0.2 to 8 percent of a concentrate solution of rapamycin in N,N-dimethylacetamide, at concentrations of rapamycin ranging from 5 mg/ml to 50 mg/ml, in combination with a diluent solution consisting essentially of 1.0 to 8 weight percent of a polyoxyethylene sorbitan ester, 10 to 50 weight percent polyethylene glycol 300 and 40 to 90 volume percent water, wherein the concentration of rapamycin in the combined solution ranges from 0.1 mg/ml to 4.0 mg/ml.

10. An aqueous, injectable rapamycin solution, said injectable solution consisting essentially of rapamycin in 0.1 to 10 weight percent N,N-dimethylacetamide, 0.09 to 7.5 weight percent of one or more polyoxyethylene sorbitan esters, 9 to 60 weight percent of either polyethylene glycol 200 or 300 or both and 30 to 90 volume percent of water, wherein the concentration of rapamycin in the solution ranges from 0.05 mg/ml to 5.0 mg/ml.

11. An aqueous, injectable rapamycin solution according to claim 10 wherein one polyoxyethylene sorbitan ester is present and the polyethylene glycol present is polyethylene glycol 300.

12. An aqueous, injectable rapamycin solution according to claim 11, for bolus injection, wherein the concentration of rapamycin in the solution ranges from 0.1 mg/ml to 4 mg/ml.

13. An aqueous, injectable rapamycin solution according to claim 11 wherein the N,N,-dimethylacetamide ranges from 0.2 to 8 weight percent of the solution.

14. An aqueous, injectable rapamycin solution according to claim 11 wherein the polyoxyethylene sorbitan ester ranges from 2 to 7.5 weight percent of the solution.

15. An aqueous, injectable rapamycin solution according to claim 11 wherein the polyethylene glycol 300 ranges from 10 to 50 weight percent of the solution.

16. An aqueous, injectable rapamycin solution according to claim 11 wherein water ranges from 30 to 90 percent by volume of the total solution.

17. An aqueous, injectable rapamycin solution according to claim 11, for bolus injection, consisting essentially of rapamycin in 2 to 8 weight percent N,N-dimethylacetamide, 2 to 7.5 weight percent of a polyoxyethylene sorbitan ester, 10 to 50 weight percent polyethylene glycol 300 and 36 to 86 volume percent of water, wherein the concentration of rapamycin in the solution ranges from 0.1 mg/ml to 4.0 mg/ml.

* * * * *